(12) United States Patent
Chu et al.

(10) Patent No.: US 7,666,439 B2
(45) Date of Patent: *Feb. 23, 2010

(54) MYCOPLASMA HYOPNEUMONIAE BACTERIN VACCINE

(75) Inventors: Hsien-Jue Chu, Fort Dodge, IA (US); Wumin Li, Fort Dodge, IA (US); Zhichang Xu, Fort Dodge, IA (US)

(73) Assignee: Wyeth LLC, Madison, NJ (US)

( * ) Notice: Subject to any disclaimer, the term of this patent is extended or adjusted under 35 U.S.C. 154(b) by 106 days.

This patent is subject to a terminal disclaimer.

(21) Appl. No.: 11/507,231

(22) Filed: Aug. 21, 2006

(65) Prior Publication Data

US 2007/0020296 A1 Jan. 25, 2007

Related U.S. Application Data

(63) Continuation of application No. 10/039,383, filed on Dec. 17, 2001, now abandoned.

(60) Provisional application No. 60/256,637, filed on Dec. 19, 2000.

(51) Int. Cl.
*A61K 39/02* (2006.01)
*A61K 39/116* (2006.01)
*A61K 39/38* (2006.01)
*A01N 63/00* (2006.01)
*A01N 65/00* (2009.01)

(52) U.S. Cl. .............. 424/264.1; 424/184.1; 424/203.1; 424/234.1; 424/93.4; 424/93.1; 424/825

(58) Field of Classification Search .............. 424/203.1, 424/184.1, 234.1, 264.1, 93.4, 93.1, 825
See application file for complete search history.

(56) References Cited

U.S. PATENT DOCUMENTS

| | | | | |
|---|---|---|---|---|
| 2,909,462 | A | | 10/1959 | Warfield et al. |
| 3,790,665 | A | | 2/1974 | Glass et al. |
| 4,606,918 | A | | 8/1986 | Allison et al. ................. 424/88 |
| 5,080,896 | A | | 1/1992 | Visser et al. ................... 424/88 |
| 5,240,706 | A | | 8/1993 | Faulds .......................... 424/92 |
| 5,338,543 | A | | 8/1994 | Fitzgerald et al. ............. 424/92 |
| 5,534,256 | A | | 7/1996 | Potter et al. ............... 424/184.1 |
| 5,565,205 | A | * | 10/1996 | Petersen et al. ........... 424/264.1 |
| 5,695,769 | A | | 12/1997 | Frantz et al. ............. 424/255.1 |
| 5,846,735 | A | * | 12/1998 | Stapleton et al. ............ 435/7.1 |
| 6,113,916 | A | * | 9/2000 | Bhogal et al. ............ 424/264.1 |
| 6,193,971 | B1 | * | 2/2001 | Hofmann et al. .......... 424/191.1 |
| 6,342,231 | B1 | | 1/2002 | Burkhardt et al. ......... 424/256.1 |
| 6,585,981 | B1 | | 7/2003 | Pijoan ...................... 424/203.1 |
| 6,753,417 | B2 | * | 6/2004 | Hansen et al. .............. 536/23.1 |
| 6,846,477 | B2 | | 1/2005 | Keich et al. ................. 424/9.1 |
| 7,018,638 | B2 | * | 3/2006 | Chu et al. ................. 424/201.1 |
| 7,169,394 | B2 | * | 1/2007 | Chu et al. ................. 424/201.1 |

| | | | |
|---|---|---|---|
| 2002/0114817 | A1 | 8/2002 | Liem et al. |

FOREIGN PATENT DOCUMENTS

| | | |
|---|---|---|
| EP | 0 283 085 A1 | 9/1988 |
| EP | 0 315 153 A2 | 5/1989 |
| WO | WO 91/18627 A1 | 12/1991 |
| WO | WO 92/03157 A1 | 3/1992 |
| WO | WO 93/10216 A1 | 5/1993 |
| WO | WO 95/30437 A1 | 11/1995 |
| WO | WO 96/40268 * | 12/1996 |
| WO | WO 02/10343 | 2/2002 |

OTHER PUBLICATIONS

Xu et al. In: Proceedings of the 17th International Pig Veterinary Society Congress, vol. 2, p. 274, Jun. 2002.*
Animal Pharm No. 422, p. 20, Jun. 4, 1999.*
Merial Marketing Information on HYORESP, Jul. 15, 1998.*
Pig Farming, p. 2, Jun. 1999.*
Baum DH. In: Proceedings of the 16th International Pig Veterinary Society Congress, Sep. 17-21, 2000, (ed) Cargill et al. Melbourne, Australia.*
Feed Stuffs 72 (30): p. 5, Jul. 17, 2000.*
ASI, No. 2918, p. 2, 1999.*
Alexander & Brewer, "Adjuvants and their modes of action," Livestock Production Science, 1995, pp. 153-162, vol. 42.
Hunter et al., "The Adjuvant Activity of Nonionic Block Polymer Surfactants," J. Immunology, Sep. 1981, pp. 1244-1250, vol. 127, No. 3.
Allison, A. C., "Squalene and Squalane Emulsions as Adjuvants," Methods, vol. 19, pp. 87-93, 1999, Academic Press Inc., NY, NY.
Goodwin et al., "Enzootic Pneumonia of Pigs: Immunization Attempts Inoculating *Mycoplasma suipneumoniae* Antigen by Various Routes and with Different Adjuvants," British Vet. J. 129(5):456-464, Sep.-Oct. 1973.
George et al.,"Route-related variation in the immunogenicity of killed *Salmonella enteritidis* vaccine: role of antigen presenting cell," Microbiol. Immunol.33(6):479-488,1989.

(Continued)

*Primary Examiner*—S. Devi
(74) *Attorney, Agent, or Firm*—Adley F. Mandel; Anne M. Rosenblum

(57) ABSTRACT

The invention provides an improved *Mycoplasma hyopneumoniae* bacterin vaccine composition, which advantageously provides immunity from infection after a single administration. The composition comprises an inactivated *Mycoplasma hyopneumoniae* bacterin and an adjuvant mixture, which, in combination, provide immunity from *Mycoplasma hyopneumoniae* infection after a single administration, and elicit an immune response specific to *Mycoplasma hyopneumoniae* bacterin and including cell-mediated immunity and local (secretory IgA) immunity. In a preferred embodiment, the adjuvant mixture comprises an acrylic acid polymer, most preferably CARBOPOL®, and a mixture of a metabolizable oil such as one or more unsaturated terpene hydrocarbons, preferably squalene or squalane, and a polyoxyethylene-polyoxypropylene block copolymer such as PLURONIC®. The vaccine composition may optionally include a preservative, preferably thimerosol and/or EDTA.

5 Claims, No Drawings

OTHER PUBLICATIONS

Byars et al., "Adjuvant formulation for use in vaccines to elicit both cell-mediated and humoral immunity," Vaccine 5:223-228, Sep. 1987.

Martinon et al.,"Efficacy of a 'One Shot' Schedule of a *Mycoplasma hyopneumoniae* Bacterin (Hyoresp)," Proc. 15th IPVS Congress, Birmingham, England, Jul. 5-9, 1998, p. 284.

Reynaud et al.,"Clinical Field Trial With *Mycoplasma hyopneumoniae* Bacterin (Hyoresp)," Proc. 15th IPVS Congress, Birmingham, England, Jul. 5-9, 1998, p. 150.

Charlier et al., "Comparative Efficacy of Stellamune Mycoplasma and Hyoresp in Pigs Against an Experimental Challenge with *Mycoplasma hyopneumoniae*," Proc. 16th IPVS Congress, Melbourne, Australia, Sep. 17-20, 2000, p. 501.

* cited by examiner

MYCOPLASMA HYOPNEUMONIAE BACTERIN VACCINE

This is a continuation application of U.S. application Ser. No. 10/039,383, filed on Dec. 17, 2001, now abandoned, which claims the priority benefit under 35 U.S.C. 119(e) of U.S. Provisional Application No. 60/256,637, filed on Dec. 19, 2000, abandoned, the entire disclosure of which is hereby incorporated by reference.

FIELD OF THE INVENTION

This invention pertains to improved methods for inducing protective immunity against *Mycoplasma hyopneumoniae*, specifically employing an inactivated *Mycoplasma hyopneumoniae* bacterin in an amount effective to immunize a recipient animal against infection by *Mycoplasma hyopneumoniae* in a single dose.

BACKGROUND OF THE INVENTION

*Mycoplasma hyopneumoniae* is the etiologic agent of swine mycoplasmal pneumonia. This disease is an important cause of economic loss in the swine industry due to reduced weight gain and poor feed efficiency. The disease causes a chronic cough, dull hair coat, retarded growth and unthrifty appearance lasting several weeks. Characteristic lesions of purple to gray areas of consolidation, particularly in ventral apical and cardiac lobes are observed in infected animals. Although the disease causes little mortality, affected swine are often prone to secondary infections by opportunistic pathogens, resulting in death or stress. Economic losses alone have been estimated at between 200 to 250 million dollars annually.

*Mycoplasma hyopneumoniae* is a slow growing, fastidious bacterium which lacks a cell wall. It is frequently difficult to isolate from the respiratory tract due to *Mycoplasma hyorhinis*, a common secondary agent also located in the respiratory tract. The disease is spread by aerosol, produced by coughing, and by direct contact from an affected or convalescent carrier swine. Mingling of infected animals and uninfected animals results in early and frequent reinfection. Infection frequently starts with infection of piglets by carrier sows at farrowing. Due to herd management techniques, infection may not become evident until later in life. Additional infection usually is observed after weaning when pigs are pooled. Overt disease is normally observed in pigs at six weeks of age or older. Grown rates and feed conversion rates are markedly reduced in affected animals. Treatments using antibiotics is expensive and require prolonged use. Reinfection is also a problem. Vaccines are presently the most effective method for avoiding infections and their consequences.

Fort Dodge Animal Health (FDAH) markets *Mycoplasma hyopneumoniae* bacterin under the name SUVAXYN® RESPIFEND° MH for use as a vaccine to protect healthy swine against clinical signs caused by *Mycoplasma hyopneumoniae*. The vaccine contains CARBOPOL® (an acrylic acid polymer) as an adjuvant and is recommended as a two-dose vaccine for pigs at least one-week old, with the second dose two to three weeks after the first vaccination. However, a two-dose vaccine has the obvious disadvantage of requiring a second handling of the animals in order to provide full protection against disease.

It is therefore an object of this invention to provide an effective vaccine against *Mycoplasma hyopneumoniae* that elicits protective immunity and prevents disease caused by this organism with an administration of a single dose of vaccine.

It is another object of this invention to provide a vaccine composition suitable for use in swine against infection and disease caused by *Mycoplasma hyopneumoniae*, and which may be used in combination with other bacterins and/or toxoids.

It is a still further object of the present invention to provide a method for the prevention or amelioration of the disease wherein the causative organism is *Mycoplasma hyopneumoniae* by utilizing an adjuvant formulation which enhances the immunogenicity of the bacterin so as to elicit protective immunity after a single dose of the vaccine.

Other objects and features of this invention will become apparent from the detailed description set forth hereinbelow.

SUMMARY OF THE INVENTION

The present invention relates to a vaccine composition for immunizing an animal against infection by *Mycoplasma hyopneumoniae* comprising an immunizing amount of an inactivated *Mycoplasma hyopneumoniae* bacterin; an adjuvant mixture comprising an acrylic acid polymer and a mixture of a metabolizable oil and a polyoxyethylene-polyoxypropylene block copolymer; and a pharmaceutically acceptable carrier, which vaccine composition, after a single administration, elicits protective immunity from *Mycoplasma hyopneumoniae*.

In another aspect, the present invention provides an immunogenic composition for immunizing an animal against infection by *Mycoplasma hyopneumoniae*, comprising an inactivated *Mycoplasma hyopneumoniae* bacterin combined with the above adjuvant mixture and a pharmaceutically acceptable stabilizer, carrier or diluent. The adjuvant is usually present in this vaccine composition at a final concentration of about 1-25% (v/v), and preferably about 5-12% (v/v). The composition may also include other vaccine components, including inactivated bacterins or purified toxoids, from one or more pathogens, such as *Haemophilus parasuis*, *Pasteurella multocida*, *Streptococcus suis*, *Actinobacillus pleuropneumoniae*, *Bordetella bronchiseptica*, *Salmonella choleraesuis* and leptospira and may be administered by intramuscular, subcutaneous, oral, aerosol or intranasal routes.

In still another aspect, the present invention provides a method for protecting an animal against disease caused by *Mycoplasma hyopneumoniae* by administering a single dose of the above-vaccine comprising inactivated *Mycoplasma hyopneumoniae* bacterin and the adjuvant mixture.

DETAILED DESCRIPTION OF THE INVENTION

All patents, patent applications, and other literature cited herein are hereby incorporated by reference in their entirety. In the case of inconsistencies, the present disclosure will prevail.

As used herein, a "bacterin" is a bacterium harvest which has been inactivated and which, in combination with certain adjuvants, can elicit protective immunity to protect against disease or infection when administered to animals.

"Adjuvant" means a composition comprised of one or more substances that enhances the immunogenicity and efficacy of *Mycoplasma hyopneumoniae* bacterin in a vaccine composition.

As used in the specification and claims, the term MHDCE designates *Mycoplasma Hyopneumoniae* DNA cell equivalents.

The "immunizing amount" is the amount of bacterin which will provide immunity vis a vis *Mycoplasma hyopneumo-* niae. The "immunizing amount" will depend upon the species, breed, age, size, health status and whether the animal has previously been given a vaccine against the same organism.

The present invention provides a vaccine against *Mycoplasma pneumoniae* that is suitable for single dose immunization. The vaccine of the present invention includes an adjuvant mixture that enhances the immunogenicity of the bacterin and thus provides for a single administration to elicit protective immunity.

The vaccine may be prepared from freshly harvested cultures by methods that are standard in the art (see, for instance, U.S. Pat. No. 5,338,543 or U.S. Pat. No. 5,565,205, as well as Example 2 below). That is, the organism may be propagated in a culture medium such as PPLO (Pleuropneumonia-like organism) complete medium [Difco]. Laboratories]. The growth of the organism is monitored by standard techniques such as determining color changing units (CCU), and harvested when a sufficiently high titer has been achieved. The stocks may be further concentrated or lyophilized by conventional methods before inclusion in the vaccine for formulation. Other methods, such as those described in Thomas, et al., Agri-Practice, Vol. 7 No. 5, pp. 26-30, can be employed.

The vaccine of the present invention comprises the inactivated *Mycoplasma hyopneumoniae* bacterin combined with the adjuvant mixture and one or more pharmaceutically acceptable carriers. Carriers suitable for use include aqueous media, for instance, saline, phosphate-buffered saline, Minimal essential media (MEM), or MEM with HEPES buffer.

The adjuvant mixture for use in the vaccine compositions of the present invention enhances the immune response and comprises a mixture of an acrylic acid polymer with a mixture of metabolizable oil, e.g., an unsaturated terpene hydrocarbon or a hydrogenation product thereof, preferably squalane (2,3,10,15,19,23-hexamethyltetracosane) or squalene, and a polyoxyethylene-polyoxypropylene block copolymer. Such an acrylic acid polymer may be a homopolymer or a copolymer. The acrylic acid polymer is preferably a carbomer. Carbomers are commercially available under the trade name CARBOPOL®. Acrylic acid polymers are described, for example, in U.S. Pat. Nos. 2,909,462 and 3,790,665, whose disclosures are incorporated herein by reference. The polyoxyethylene-polyoxypropylene block copolymers are surfactants, preferably liquid surfactants, that aid in suspending solid and liquid components. The surfactants are commercially available as polymers under the trade name PLURONIC®. The preferred surfactant is poloxamer 401 which is commercially available under the trade name PLURONIC® L121.

The immunogenically stimulating adjuvant mixture is typically present in the vaccine composition of the invention in v/v amounts of about 1% to 25%, preferably about 2% to 15%, more preferably about 5% to 12% v/v. The amount of adjuvant mixture use and the ratio of the two components of the adjuvant may vary depending upon the addition of other bacterins or purified toxoids. The adjuvant mixture generally comprises a metabolizable oil, an acrylic acid polymer and a polyoxyethylene-polyoxypropylene block copolymer formulated as an emulsion in an aqueous medium.

In this adjuvant mixture, the metabolizable oil and the acrylic acid polymer may be present in amounts ranging from about 10 to 150 ml/L and about 0.5 to 10 g/L, respectively. In a preferred embodiment of the adjuvant mixture, the mixture of the metabolizable oil and polyoxyethylene-polyoxypropylene block copolymer component is a mixture of squalane and PLURONIC® L121 (poloxamer 401) which may be present in an amount of about 50 to 100 ml/L and the carboxymethylene polymer is CARBOPOL® 934P (Carbamer 934P) which may be present in amount of about 2 ml/L. Typically, the adjuvant mixture contains about a 1:25 to 1:50 ratio of acrylic acid polymer to metabolizable oil/polyoxyethylene-polyoxypropylene block copolymer mixture.

Preferred acrylic acid polymers are those marketed by B. F Goodrich as CARBOPOL® 934 P NF and 941 NF which are polymers of acrylic acid cross-linked with polyallylsucrose and which have the chemical formula $(CH_2CHOOOH)_n$. These polymers form aqueous gels which suitably formulate with aqueous carriers. Preferred polyoxyethylene-polyoxypropylene block copolymers are the nonionic surfactants marketed by BASF as PLURONIC® L121, L61, L81 or L101.

The vaccine of the present invention may be administered by intramuscular, subcutaneous, intranasal, intraperitoneal or oral routes, preferably by intramuscular or subcutaneous routes.

The vaccine of the invention generally comprises the inactivated *Mycoplasma hyopneumoniae*, a metabolizable oil, a polyoxyethylene-polyoxypropylene block copolymer and an acrylic acid polymer in the form of an oil in water emulsion. The vaccine preferably contains the acrylic acid polymer in a concentration within the range of 0.5 to 10 g/L. The vaccine preferably contains the metabolizable oil in a concentration within the range of 2 to 6 ml/L. The vaccine preferably contains the polyoxyethylene-polyoxypropylene block copolymer in a concentration within the range of 1 to 3 ml/L.

For single-dose administration, the vaccine should preferably contain an amount of *Mycoplasma hyopneumoniae* bacterin corresponding to about $1\times10^8$ to $3\times10^{11}$ MHDCE/mL, preferably about $1\times10^9$ to $3\times10^9$ MHDCE/mL. About one to five mL, preferably 2 mL, may be administered per animal, intramuscularly, subcutaneously, or intraperitoneally. One to ten mL, preferably 2 to 5 mL, may be administered orally or intranasally.

The following examples are intended to further illustrate the invention without limiting its scope.

EXAMPLE 1

*Mycoplasma hyopneumoniae* Bacterin Preparation of the Vaccine Composition

DESCRIPTION OF VIRAL STOCKS. *Mycoplasma hyopneumoniae* may be obtained from any number of readily available sources. In one embodiment, *Mycoplasma hyopneumoniae* Strain P-5722-3 may be used. The culture was obtained from C. Armstrong, Purdue University, West Lafayette, Ind. Following receipt of the *Mycoplasma hyopneumoniae* culture, it was passed in *Mycoplasma hyopneumoniae* broth seven times to establish the Master Seed.

CELL CULTURE. *Mycoplasma hyopneumoniae* was grown in a medium comprising Bacto PPLO Powder, yeast extract, glucose, L-cysteine hydrochloride, ampicillin, thallium acetate, phenol red, antifoam, normal sterile swine serum and water over periods ranging from 18-144 hours. For inactivation, binary ethyleneimine (BEI) is added directed to the production culture within the fermentation vessel. The pH is adjusted to 7.4, and then harvested according to conventional procedures to provide *Mycoplasma hyopneumoniae* bacterin.

Preparation of the Vaccine Composition

Composition of Preservatives and Proportions Used. The harvested bacterin is preserved by the addition of thimerosal and ethylene diaminete tetra-acetic acid, tetra-sodium salt (EDTA) at no more than 0.01% and 0.07%, respectively.

Ampicillin U.S.P. is present in the growth medium at 0.250 grams/liter. The concentration of residual ampicillin will vary in the final product depending on the volume of harvest fluids, with the residual ampicillin concentration in the completed product not exceeding 30 ug/mL.

STANDARDIZATION OF THE PRODUCT. The *Mycoplasma* concentrate is quantitated by a DNA Fluorometric Assay.

A mixture of a metabolizable oil that comprises one or more terpene hydrocarbons and a polyoxyethylene-polyoxypropylene block copolymer, e.g., a Squalane/PLURONIC® L121 mixture, is prepared by dissolving 10 g. sodium chloride, 0.25 g potassium chloride, 2.72 sodium phosphate dibasic, 0.25 potassium phosphate monobasic, 20 mL PLURONIC® L121 (BASF Corporation), 40 mL Squalane (Kodak), 3.2 mL TWEEN® 80 (polysorbate 80) in 900 mL purified water, q.s. to 1000 ml. After mixing, the ingredients may be autoclaved. The mixture is then homogenized until a stable emulsion is formed. Formalin may be added up to a final concentration of 0.2% or thimerosal may be added to a final concentration of 1:10,000.

ASSEMBLY OF UNITS TO MAKE A SERIAL. Satisfactory *Mycoplasma hyopneumoniae* concentrates are aseptically combined with the adjuvants, preservative, and diluent into a sterile container equipped with an agitator and mixed for no less than 30 minutes.

| Amounts for 1,000,000 doses (2 mL each): | | % vol/vol |
|---|---|---|
| *Mycoplasma* Concentrate (>1.0 × $10^{10}$ MHDCE/mL) | 400,000 mL | 20.0 |
| Squalane/PLURONIC ® L121 mixture | 100,000 mL | 5.0 |
| CARBOPOL ® (2% w/v in water) | 200,000 mL | 10.0 |
| Thimerosal Solution 1% w/v in water and EDTA (tetrasodium salt) 7 w/v % | 18,000 mL | 0.9 |
| Sterile Saline | 1,282,000 mL | 64.1 |

The pH of the serial is adjusted to 7.0 ± 0.2.
MHDCE = *Mycoplasma hyopneumoniae* DNA Cell equivalents METHOD AND TECHNIQUE OF FILLING AND SEALING OF FINAL CONTAINERS. The product may be gross filtered through a sterile 200-500 micron filter element and filled under conditions specified in 9 CFR 114.6 into sterile final containers in a room designated for filling operations. The glass or plastic containers are closed with a rubber stopper and crimpt sealed with aluminum seals. Each 2.0-mL dose will contain no less than $2\times10^9$ *Mycoplasma hyopneumoniae* DNA Cell equivalents.

TESTING FOR POTENCY. Bulk or final container samples of the completed product can be potency-tested as follows:

Assay Method for Potency Testing: ICR female mice, six to seven weeks of age, of one consignment, from Harlan Sprague Dawley or other acceptable suppliers, are used. A minimum of 20 mice are required for immunization with each Unknown and Reference bacterin. A minimum of five mice are retained as non-inoculated controls. Test and reference bacterins are individually mixed thoroughly. Sterile, disposable syringes, fitted with 25-gauge by ⅝ inch needles, are used to inoculate the mice subcutaneously in the inguinal region with $1/10^{th}$ of a host animal dose (0.2 mL). Each group of mice is housed as an individual unit and allowed free access to food and water for 14 days. Each mouse is then anesthetized. The anesthetized mouse is placed on its back. Using one hand, the head is held down and one front leg is extended away from the body. Using a scalpel, a skin incision is made approximately ½-inch long between the extended front leg and thorax, severing the brachial artery. Using a 3.0 mL syringe, without needle, the blood which is pooled in the incision, is collected. The blood discharged into a labeled test tube and is allowed to clot. The clotted tubes are centrifuged at 1,000×g to separate the serum from the clot. Individual serums are stored at −20° C. or colder until tested.

SEROLOGICAL TESTING: An ELISA Procedure is used to measure the antibody response of mice to the Reference and/or Unknown bacterins. The ELISA Procedure is conducted using Disposable IMMULON II Flat-Bottom Microtiter Plates from Dynatech or equivalent and an ELISA Plate Reader.

Test Reagents:

Phosphate Buffered Saline-TWEEN® (PBST) (pH adjusted to 7.2 to 7.4 with 5N NaOH or 5N HCl).

| | Amount Per Liter | |
|---|---|---|
| Ingredients | Liter | |
| NaCl | 8.50 | grams |
| $NaH_2PO_4$ | 0.22 | grams |
| $Na_2HPO_4$ | 1.19 | grams |
| TWEEN ®-20 | 0.50 | ml |
| Deionized Water q.s. | 1,000.00 | ml |

Glycine Buffered Saline (GBS) (pH adjusted to 9.5 to 9.7 with 5N NaOH or 5N HCl).

| Ingredients | Amount Per Liter | |
|---|---|---|
| Glycine | 0.75 | grams |
| NaCl | 8.50 | grams |
| Deionized Water q.s. | 1,000.00 | ml |

Positive Control Serum: The Positive Control Serum is a pool of serums from mice vaccinated with *Mycoplasma hyopneumoniae* bacterin.

Conjugate and Substrate:

Affinity-Purified Anti-Mouse IgG Peroxidase-Labeled conjugate is obtained from Kirkegaard and Perry Laboratories, Inc. (Catalog No. 074-1802). The procedure for determining the optimal dilution of conjugate is detailed below. The Peroxidase Substrate Solutions (ABTS) are obtained from Kirkegaard and Perry, Inc.

Titration of Conjugate: An IMMULON II Flat-Bottom Plate is coated with 100 ul per well of 20 ug per mL *Mycoplasma hyopneumoniae* Whole Cell Antigen diluted in 10 mM GBS. The plate is incubated for no less than one hour at 37° C.+2° C. and is transferred to 2-7° C. for no less than 18 hours and no more than one week. Prior to using the plate is washed three times with PBST, with a one-minute soaking time between each wash, and is tapped to dry. A 1:40 dilution in PBST of the Positive Control Serum is prepared, and the diluted Positive Serum (100 uL/well) is added to one-half of the wells in the plate. PBST is added to the other one-half of the wells. The plate is incubated for one hour at room temperature, after which the plate is washed three times. The conjugated serum is serially diluted with PBST two-fold, starting with a 1:100 dilution and ending with a 1:10,240 dilution. 100 ul of each conjugate dilution is added to four wells of the Positive Serum and four wells of the PBST, and is allowed to react for one-half hour at room temperature. The plates are washed four times, and 100 ul of the Peroxidase Substrate Solution (abts) is added per well. The plate is read at a dual wavelength setting of T λ=450. A dilution of Conjugate is chosen that gives a reading of 0.850 to 1.050 for the Positive Control Serum when the value of the PBST Control is subtracted from the value of the Positive Control Serum.

Test Antigen:

*Mycoplasma hyopneumoniae* Antigen is a whole cell preparation, and is supplied by Fort Dodge Animal Health.

The ELISA is performed as follows: Dynatech IMMULON II Flat-Bottom Microtiter Plates are used. One vial of Lyophilized *Mycoplasma hyopneumoniae* Whole Cell Antigen is reconstituted to ten ml with Glycine Buffered Saline (GBS). The concentration of the reconstituted *Mycoplasma* Protein is 20 µg/mL. 100 µl (2 µg) of diluted antigen is then added to all wells of a plate. The plate is incubated at 37° C.±2° C. for no less than one hour and then transferred to 2-7° C. for a minimum of 18 hours and a maximum of one week. The plates are washed three times with PBST, soaking one minute between each wash, and are then tapped dry. Serums are diluted 1:40 in PBST. The Positive Control Serum will be included in quadruplicate on every plate. Sample volume per well is 100 µl. Serial Test Serum Samples and Reference Serum Samples will be tested in duplicate on the same plate. The plates are incubated for one hour at room temperature, and are washed three times with PBST. 100 µl of Anti-Mouse IgG Peroxidase-Labeled Conjugate (Kirkegaard and Perry), diluted in PBST is added to all wells, and the wells are incubated for 30 minutes at room temperature. The plates are washed four times with PBST. 100 µl of a Peroxidase Substrate Solution (ABTS) is added to all wells, and the plates are incubated until the Positive Serum Control reaches an $OD_{405}$ (450) of 0.850 to 1.050 when the machine is blanked against the PBST Control Wells. The plates are read, and are blanked against the PBST Wells. To be a valid test, the sera of mice inoculated with the Reference Bacterin must produce a minimum average value of 0.500, and the sera of the non-vaccinated control mice must not exceed the maximum average value of 0.100. Or, the difference between the average value of the sera of mice inoculated with the Reference Bacterin and the sera of the non-vaccinated control mice must be greater than or equal to 0.400.

The Mean Values for the Serial Vaccinates, the Reference Vaccinates, and the Controls, are calculated and evaluated as follows: To be considered satisfactory, the Test Bacterin must demonstrate an average Mean Optical Density Value equal to, or greater than, the Reference. Or, using a One-Tailed Student's T-Test, the Test Bacterin must not be significantly ($p \leq 0.05$ Confidence Level) lower than the Reference Bacterin. Any calculated T-Value equal to, or greater than, 1.686 will indicate a significant difference between the Reference and Test Bacterin, and will cause the Test Bacterin to be rejected. Any calculated T-Value less than 1.686 will indicate a satisfactory serial. Any test bacterin determined by the Test to be unsatisfactory for any reason unrelated to product efficacy is re-tested, and the initial test is regarded as invalid.

EXAMPLE 2

Test Vaccine:

The vaccine for testing was prepared according to the procedures detailed in Example 1 using 5% of a mixture of a metabolizable oil that comprises one or more terpene hydrocarbons and a polyoxyethylene-polyoxypropylene block copolymer (Squalane/PLURONIC® L121 mixture) and 0.2% acrylic acid polymer (CARBOPOL®) as adjuvant, and $2\times10^9$ *M. hyopneumoniae* DNA cell equivalents (MHDCE) per dose.

EXAMPLE 3

This study was designed to demonstrate four months duration of immunity (DOI) in pigs induced by one-dose vaccination of the vaccine of Example 2 at an age of three weeks.

Two separate animal trials were carried out for this study. All pigs in both trials were sero-negative (antibody titer<10) at the time of vaccination, indicating the animals were susceptible to *Mycoplasma hyopneumoniae*. All pigs in the control groups remained sero-negative before challenge. This indicates that the immune response in the vaccinated pigs was due to the vaccine and not to any environmental exposure.

In the first trial, a vaccine of Example 2 was evaluated together with a commercially available product, INGELVAC M. HYO® manufactured by Boehringer Ingelheim (BI), by a high level of virulent *M. hyopneumoniae* ($0.4\times10^6$ organisms) challenge. Twenty-two (22) pigs at the age of 18-21 days were vaccinated with the vaccine of Example 2 intramuscularly (IM) and eight (8) pigs with the INGELVAC M. HYO® [serial 271 032]. Twenty-two (22) pigs served as challenge controls and 10 pigs as non-challenge controls. The pigs in the vaccinated and challenge control groups were challenged with virulent *M. hyopneumoniae* at four months after vaccination. The pigs vaccinated with the vaccine of Example 2 had average lung lesions of 15.9% and the challenged control pigs had average lung lesions of 19.6%. The average lung lesions in the group vaccinated with the vaccine of Example 2 were less than the controls even though the pigs had been challenged with a higher dose than that recommended by Iowa State University (ISU), however, the difference was not significant (p=0.19). Likewise, when the commercial product, INGELVAC M. HYO® was evaluated in the same group of animals with the same dose of challenge, a similar level of lung lesions was also observed (14.6%). There was also no significant difference between the INGELVAC M. HYO® vaccinated group and the control group (p=0.27) and between the INGELVAC M. HYO® vaccinated group and the group vaccinated with the vaccine of Example 2.

In the second trial, a vaccine of Example 2 was evaluated by virulent *M. hyopneumoniae* challenge at the level suggested by ISU ($1.0\times10^6$ organisms) at four months after the vaccination. Twenty-three (23) pigs were vaccinated with one dose of the vaccine at the age of 21 days, 25 pigs served as challenge controls and 7 pigs as non-challenge controls. The pigs in the vaccinated and challenge control groups were challenged with virulent *M. hyopneumoniae* at four months after vaccination. The control group had average lung lesions of 10.4% and the vaccinated group had average lung lesions of 5.5%. There was a significant difference between the vaccinated group and the control group (p=0.031). This indicates that the vaccine of Example 2 is efficacious in stimulating protective immunity, which can last at least four months after a single dose vaccination in pigs at the age of three weeks.

When the data related to the vaccine of Example 2 in the two trials were combined and analyzed, the average lung lesions of the vaccinated group were significantly lower than that of the control group.

In conclusion, the vaccine of Example 2 induces protective immunity against the virulent *M. hyopneumoniae* challenge at four months after one-dose vaccination in pigs at the age of three weeks.

Experimental Data Two separate trials were conducted in this study. In trial one, sixty-seven (67) pigs were assigned into four groups using the Microsoft Excel randomization program. Twenty-four (24) pigs were vaccinated with one dose of a vaccine prepared according to Example 2 intramuscularly (IM) at the age of 18-21 days. Twenty-four (24) pigs served as challenge controls and 10 pigs as non-challenge controls. Nine pigs were vaccinated IM with the commercial product, INGELVAC M. HYO®, [serial 271 032, manufactured by Boehringer Ingelheim (BI)], per label instruction. Five pigs (two pigs vaccinated with the vaccine of Example 2, one with the BI vaccine and two controls) died during the vaccination holding period due to reasons not related to the vaccination. The remaining pigs in the vaccinated groups and challenge control group were challenged with 14 mL of virulent $M.$ $hyopneumoniae$ ($1.4 \times 10^6$ organisms) at four months after the vaccination. The pigs in all four groups were euthanized 30 days after the challenge and lung lesions were scored for each pig in the trial.

In a second trial, twenty-five (25) pigs were vaccinated IM with one dose of a vaccine prepared according to Example 2 at the age of 21 days. Twenty-five (25) pigs served as challenge controls and 10 pigs as non-challenge controls. Two pigs dies due to reasons not related to the vaccination and one pig was mistakenly sold during the vaccination holding period. The remaining pigs in the vaccinated and challenge control groups were challenged with 10 mL of virulent $M.$ $hyopneumoniae$ ($1.0 \times 10^6$ organisms) at four months after the vaccination. Two pigs died during the post challenge observation period due to reasons not related to the vaccination/challenge. The remaining pigs in all three groups were euthanized 30 days after the challenge and lung lesions were scored for each pig in the trial.

Vaccination:

Each pig in the vaccination groups was given one 2 mL dose of the test vaccines IM in the side of the neck.

Challenge and Necropsy:

The virulent $M.$ $hyopneumoniae$ challenge stock, a frozen (−70° C.) lung homogenate was prepared by Dr. Eileen Thacker from Iowa State University (ISU). The challenge stock was confirmed to be pure and contained approximately $10^7$ $M.$ $hyopneumoniae$ organisms per mL. The recommended challenge dose is 10 mL of a 1:100 diluted stock (i.e., $1.0 \times 10^6$ organisms).

The pigs in the vaccinated and challenge control groups in the first trial were challenged with 14 ml of 1:100 diluted stock (i.e. $1.4 \times 10^6$ organisms). The pigs in the second trial were challenged with 10 mL of 1:100 diluted stock (i.e., $1.0 \times 10^6$ organisms) as recommended.

On the day of challenge, the homogenate was thawed rapidly under warm water and diluted according to recommendations by ISU using sterile $M.$ $hyopneumoniae$ growth medium. Pigs were sedated with a mixture of xylazine-ketamine-TELAZOL® consisting of 50 mg/mL xylazine, 50 mg/mL ketamine, and 100 mg/mL TELAZOL® (an anesthetic agent and minor tranquilizer containing tiletamine hydrochloride 50 mg/mL and zolazepam hydrochloride 50 mg/mL). The anesthetic mixture was given IM at 0.01-0.02 mL/lb. body weight. Each pig was given a single 14 mL (first trial) or 10 mL dose (second trial) of the challenge material, intra-tracheally. To ensure needle placement was correct, air was drawn into the syringe prior to administration of the challenge dose. The non-vaccinated non-challenged control pigs were maintained in separate rooms and not challenged.

At 30 days post challenge (DPC), all pigs were euthanized. Lungs were removed and the gross lung lesions were scored by an individual with no knowledge of the test groups.

Sample Collection and Testing:

Blood samples were collected from all pigs on the day of vaccination (0 DPV), at one month post vaccination (1 MPV), 4 MPV/0 DPC, and 30 DPC for serum antibodies against $M.$ $hyopneumoniae$ as detected by a competitive ELISA kit (made by DAKO Co.). The serum samples were stored at −20° C. prior to being tested.

Data Analysis:

Lung lesion scores were compared between vaccinated and non-vaccinated groups by analysis of variance (ANOVA). Lung scores were arcsine transformed to improve the distribution of the residuals.

Results and Discussion

Serology: All pigs in both trials were tested for serum antibodies against $M.$ $hyopneumoniae$ by a commercial competitive ELISA kit, using a 1:10 serum dilution for all testing. All pigs were seronegative (antibody titer<10) at the time of vaccination, indicating the animals were susceptible to $M.$ $hyopneumoniae$. All pigs in the control groups remained seronegative before challenge. This indicates that the immune response in the vaccinated pigs was due to the vaccine and not to any environmental exposure. All pigs in the vaccinated groups and most of the pigs in the challenge control groups (18 out of 22 pigs in trial one and 15 out of 25 in trial two) sero-converted to $M.$ $hyopneumoniae$ after the challenge while all non-challenged animals remained sero-negative. This implies that the challenge was $M.$ $hyopneumoniae$ specific. The serological status of the test animals is summarized in Table 1.

Immunogenicity Testing in the First Trial:

The first trial was conducted to determine if the vaccine of Example 2 could stimulate strong immunity which could protect against a higher level of challenge than that recommended by ISU at four months after the vaccination. This trial also compared a vaccine of Example 2 with the commercially available, INGELVAC M. HYO®, for its ability to stimulate protective immunity at four months after vaccination.

Twenty-two pigs vaccinated with FDAH SUVAXYN® MH-One and eight pigs with a licensed product, INGELVAC M. HYO® serial 271,032, were challenged with $1.4 \times 10^6$ organisms per pig of the challenge material ($1.0 \times 10^6$ organisms per pig was recommended by ISU, see Section 5.5). Twenty-two pigs served as challenge controls and 10 pigs as non-challenge controls. The percentages of lung lesions are summarized in Table 2. The pigs vaccinated with the vaccine of Example 2, had average lung lesions of 15.9% and the challenged control pigs had average lung lesions of 19.6%. The lung lesions in the group vaccinated with the vaccine of Example 2 were less than the control even when the pigs were challenged with a higher dose of $M.$ $hyopneumoniae$. However, the difference was not significant (p=0.19). Likewise, when a commercially available product, INGELVAC M. HYO® was evaluated in the same group of animals with the same dose of challenge, a similar level of lung lesions was also obtained (14.6%). There was no significant difference between the INGELVAC M. HYO® vaccinated group and the control group (p=0.27) and between the INGELVAC M. HYO® vaccinated group and the group vaccinated with the vaccine of Example 2 (p=0.88).

Although a non-significant numerical reduction in lesions was recorded in the group receiving the vaccine of Example 2, the data obtained in this trial suggest that the higher challenge dose ($1.4 \times 10^6$ organisms) used in this trial was probably overwhelming, even to the immunity of the pigs stimulated by the commercial Ingelvac product. This challenge level is probably not appropriate for the vaccination/challenge study evaluation using group sizes of 20-25 animals, although with larger group sizes it is possible that signficance could be proven.

Immunogencity Testing in the Second Trial:

The pigs in the vaccinated and challenge control groups in trial two were evaluated with the challenge dose ($1.0 \times 10^6$ organisms) as recommended by ISU at four months after vacination to demonstrate four months DOI. The percentages of lung lesion are summarized in Table 3. The control group had an average lung lesion of 10.4%. The vaccinated group had the average lung lesion of 5.5%. There is a significant difference between the vaccinated and the control groups (p=0.031). This indicates that the vaccine of Example 2 is efficacious in stimulating protective immunity, which can last at least four months after a single dose vaccination in pigs at the age of three weeks.

Evaluation of the Combined Results of Both Trials:

While two trials were significantly different, the effect of trial on group was not significant. The magnitude of the effect of group was similar between the two trials. Thus, the effect of group could be evaluated without considering trial. Since the analysis of the full model showed that the interaction between group and trial was not significant, this supports the notion that the effect of group was the same in both trials and justifies the combination of data from the two trials into a single analysis. As such when the data related to the vaccine of Example 2 from the two trials was combined and the arcsine transformed variable for lung lesion was analyzed with group and trial as independent variables (reduced model), the group is statistically significant (p=0.013).

TABLE 1

Summary of serological status to *M. hyopneumoniae* in control and vaccinated pigs

| Trial one | Number | Positive/negative (1:10) at | | |
|---|---|---|---|---|
| Group | of pigs | ODPV | −1DPC | 30DPC |
| FDAH vaccine | 22 | 0/22 | 0/22 | 22/22 |
| BI vaccine | 8 | 0/8 | 4/8 | 8/8 |
| Challenge Control | 22 | 0/22 | 0/22 | 18/22 |
| Non-Challenge Control | 10 | 0/10 | 0/10 | 0/10 |

| Trial two | Number | Positive/negative (1:10) at | | |
|---|---|---|---|---|
| Group | of pigs | ODPV | −3DPC | 30DPC |
| FDAH vaccine | 23 | 0/23 | 6/23 | 23/23 |
| Control | 25 | 0/25 | 0/25 | 14/25 |
| Non-Challenge Control | 7 | 0/7 | 0/7 | 0/7 |

TABLE 2

Summary of percentages of lung lesion in trial one (over-dose)*

| Group | Number of pigs | Average percentages of lung lesion | P-value |
|---|---|---|---|
| FDAH vaccine | 22 | 15.90% | 0.19** |
| BI vaccine | 8 | 14.60% | 0.27*** |

TABLE 2-continued

Summary of percentages of lung lesion in trial one (over-dose)*

| Group | Number of pigs | Average percentages of lung lesion | P-value |
|---|---|---|---|
| Control | 22 | 19.60% | |
| Non-Challenge Control | 10 | 0% | 0.88**** |

*Pigs were challenged with $1.4 \times 10^6$ organisms per pig (ISU recommended dose $1.0 \times 10^6$ organisms per pig)
**comparison between FDAH vaccine group and control group
***comparison between BI vaccine group and control group
****comparison between BI vaccine group and FDAH vaccine group

TABLE 3

Summary of percentages of lung lesion in trial two (recommended dose)

| Group | Number of pigs | Average percentages of lung lesion | P-value |
|---|---|---|---|
| FDAH vaccine | 23 | 5.50% | 0.031** |
| Control | 25 | 10.40% | |
| Non-Challenge Control | 7 | 0.77% | |

* Pigs were challenged with ISU recommended dose ($1.0 \times 10^6$ organisms per pig)
**comparison between FDAH vaccine group and control group

EXAMPLE 4

Evaluation of the Long-term Immunity Induced by a Vaccine Composition of the Invention Against a Virulent Challenge Six Months After a Single-dose Administration Using essentially the same procedures described in Examples 1 and 2 and employing the amounts shown below, test vaccine A was prepared.

Test Vaccine A

| Amounts for 1,000,000 doses (2 mL each): | | | % vol/vol |
|---|---|---|---|
| *Mycoplasma* Concentrate ($>1.0 \times 10^{10}$ MHDCE/ml) | 1200,000 | mL | 60.0 |
| Squalane/PLURONIC ® L121 mixture | 200,000 | mL | 10.0 |
| CARBOPOL ® (2% w/v in water) | 200,000 | mL | 10.0 |
| Thimerosal Solution 1% w/v in water and EDTA (tetrasodium salt) 7 w/v % | 18,000 | mL | 0.9 |
| Sterile Saline | 382,000 | mL | 19.1 |

The pH of the serial is adjusted to 7.0 ± 0.2.
MHDCE = *Mycoplasma hyopneumoniae* DNA Cell equivalents Summary Thirty-three 21-day pigs were enrolled in this evaluation. Twenty pigs were vaccinated with one dose of vaccine A intramuscularly (IM) at the age of three weeks. Ten pigs served as non-vaccinated controls and three pigs as non-challenge environmental controls.

All pigs were sero-negative (antibody titer<10) at the time of vaccination, indicating the animals were susceptible to *M. hyopneumoniae*. All pigs in the control groups remained sero-negative before challenge. This indicates that the immune response in the vaccinated pigs was due to the vaccine and not to any environmental exposure.

Six months following vaccination, 20 vaccinated pigs and 10 non-vaccinated control pigs were challenged with virulent *M. hyopneumoniae* ($1.0 \times 10^6$ organisms per pig). Three pigs served as non-challenged controls. The vaccinated pigs had an average lung lesion score of 3.6% and the challenged control pigs had an average lung lesion score of 14.6%. The lung lesions in the vaccinated group were significantly less than that in the controls (p=0.0215).

The data obtained in this evaluation demonstrate that test vaccine A induced long term protective immunity against the virulent *M. hyopneumoniae* challenge six months after a single dose vaccination.

Experimental Design

Thirty-three 21 day old pigs were randomly assigned into three groups (vaccinated group, challenge control group and non-challenge environmental control group) using the Microsoft Excel randomization program by litter. Twenty pigs were vaccinated with one dose of test vaccine A intramuscularly at the age of three weeks. Ten pigs served as challenge controls and three pigs as non-challenge environmental controls. The pigs in the vaccinated group and the challenge controls were challenged with 10 mL of a virulent *M. hyopneumoniae* ($1.0 \times 10^6$ organisms) culture per pig at six months after vaccination. Three non-vaccinated pigs were used as non-challenge controls. The challenged pigs and non-challenged controls were euthanized 26 days after challenge and lung lesions scored for each pig.

Each pig in the vaccination groups was given one 2 mL-dose of the test vaccine IM in the side of the neck.

Challenge and Necropsy

The virulent *M. hyopneumoniae* challenge stock, a frozen ($\leq -70°$ C.) lung homogenate, was prepared by Dr. Eileen Thacker from Iowa State University (ISU). The challenge stock was confirmed to be pure and contained approximately $10^7$ *M. hyopneumoniae* organisms per mL.

The pigs were challenged with 10 mL of a 1:100 dilution of the stock (i.e., approximately $1.0 \times 10^6$ organisms).

On the day of challenge, the homogenate was thawed rapidly under warm water and diluted according to recommendations by ISU using sterile *M. hyopneumoniae* growth medium. Pigs were sedated with a mixture of xylazine-ketamine-TELAZOL® consisting of 50 mg/mL xylazine, 50 mg/mL ketamine, and 100 mg/mL TELAZOL® (an anesthetic agent and minor tranquilizer containing tiletamine hydrochloride 50 mg/mL and zolazepam hydrochloride 50 mg/mL). The anesthetic mixture was given IM at 0.01-0.02 mL/lb body weight. Each pig was given a single 10 mL dose of the challenge material ($1.0 \times 10^6$ organisms), intra-tracheally. To ensure needle placement was correct, air was drawn into the syringe prior to administration of the challenge dose. The non-vaccinated non-challenged control pigs were maintained in separate rooms and not challenged.

At 26 days post challenge (DPC), all pigs were euthanized. Lungs were removed and the gross lung lesions were scored as described in Example 3.

Sample Collection and Testing

Blood samples were collected from all pigs on the day of vaccination (0 DPV), at 35 DPV, −1 DPC and 26 DPC for the determination of serum antibodies against *M. hyopneumoniae* as detected by a competitive ELISA kit (made by DAKO Co.). The serum samples were stored at $\leq -20°$ C. prior to being tested.

Data Analysis

Lung lesion scores were compared between vaccinates and controls by one-way ANOVA. The lung lesion scores were arc sine transformed to improve the distribution of the residuals. Since the normality assumption for the lung lesion scores was questionable, both the lung lesion scores and the arc sine transformed lung lesion scores were analyzed by Wilcoxon Rank Sum test. The level of significance was set at p<0.05. The results from the non-parametric, Wilcoxon Rank Sum test were used for reporting purposes.

Results and Discussion

Serology

All pigs were tested for serum antibodies against *M. hyopneumoniae* by a commercial competitive ELISA kit, using a 1:10 serum dilution for all testing. The samples with test result suspicious per kit instructions are treated as positive in data analysis. All pigs were sero-negative (antibody titer<10) at the time of vaccination, indicating the animals were susceptible to *M. hyopneumoniae*. All pigs in the control groups remained sero-negative before challenge. After vaccination, fifteen of twenty vaccinates (15/20) became sero-positive to *M. hyopneumoniae* at least once (samples collected at 35 DPV and −1 DPC). This indicates that the immune response in the vaccinated pigs was due to the vaccine and not to any environmental exposure. All vaccinated pigs and four of ten pigs in the challenge control group became sero-positive to *M. hyopneumoniae* after the challenge while all non-challenged animals remained sero-negative. The serological status of the test animals is summarized in Table 4.

Lung Lesion Scores

Twenty pigs vaccinated with Test Vaccine A and ten non-vaccinated control pigs were challenged with virulent *M. hyopneumoniae* ($1.0 \times 10^6$ organisms per pig) at six months after vaccination. Three pigs served as non-challenged controls. Eight of twenty vaccinates (40%) did not develop lung lesions after the challenge whereas in the control group only one of 10 pigs (10%) did not have lung lesion. The percentages of lung lesions are summarized in Table 5. The vaccinated pigs had an average lung lesion score of 3.6% and the challenged control pigs had an average lung lesion score of 14.6%. The lung lesions in the vaccinated group were significantly less than the controls (p=0.0215).

TABLE 4

Serological status to *M. hyopneumoniae* of the pigs in the study*

| | | | Number of Positive (1:10)/total | | | |
|---|---|---|---|---|---|---|
| Group | Treatment | Number of pigs | 0 DPV** | 35 DPV | −1 DPC*** | 26 DPC |
| 1 | Vaccine/challenge | 20 | 0/20 | 9/20 | 12/20 | 20/20 |
| 2 | Control/challenge | 10 | 0/10 | 0/10 | 0/10 | 4/10 |
| 3 | Control/no challenge | 3 | 0/3 | 0/3 | 0/3 | 0/3 |

*The serum samples were tested for serum antibodies to *M. hyopneumoniae* by ELISA using a commercial kit.
All samples were tested at serum dilution 1:10. Results were interpreted per kit instructions.
Sample suspicious at 1:10 were considered positive.
**DPV = day post vaccination
***DPC = day post challenge

TABLE 5

Summary of lung lesion scores (%) in pigs challenged with
M. hyopneumoniae and in unchallenged controls

| Group | Treatment | Number of pigs | Mean % lung lesion scores | Standard Deviation | Lower 95% CL* for Mean | Upper 95% CL for Mean | P value** |
|---|---|---|---|---|---|---|---|
| 1 | Vaccine/challenge | 20 | 3.6 | 7.6 | 0.07 | 7.19 | 0.0215 |
| 2 | Control/challenge | 10 | 14.6 | 20.0 | 0.33 | 28.94 | |
| 3 | Control/no challenge | 3 | 1.8 | 1.8 | −2.67 | 6.27 | |

*CL = confidence level
**The P value was from the comparasion of groups 1 and 2.

As can be seen from the data shown in Tables 4 and 5, Test Vaccine A induces protective immunity against a virulent *M. hyopneumonia* challenge for six months after a single dose administration in pigs vaccinated at the age of three weeks.

What is claimed is:

1. A vaccine composition for immunizing a porcine animal against infection by *Mycoplasma pneumoniae* which comprises
    an immunizing amount of *Mycoplasma pneumoniae* bacterin;
    an adjuvant mixture comprising an acrylic acid polymer and a mixture of a metabolizable oil and a polyoxyethylene-polyoxypropylene block copolymer; and
    a pharmaceutically acceptable carrier, wherein said vaccine composition, after a single dose administration, elicits protective immunity lasting for six months in said porcine animal against said *Mycoplasma pneumoniae* infection.

2. The vaccine composition of claim 1 wherein the adjuvant mixture comprises about 1-25% v/v of the vaccine composition.

3. The vaccine composition of claim 1, wherein the metabolizable oil is squalane or squalene.

4. The vaccine composition of claim 3, wherein the acrylic acid polymer is a polymer of acrylic acid cross-linked with polyallylsucrose having the chemical formula $(CH_2CHOOOH)_n$.

5. The vaccine composition as in any of claims 1, 2, 3 or 4, further comprising at least one bacterin selected from the group consisting of *Haemophilus parasuis, Pasteurella multocida, Streptococcus suis, Actinobacillus pleuropneumoniae, Bordetella bronchiseptica, Salmonella choleraesuis* and leptospira.

* * * * *

UNITED STATES PATENT AND TRADEMARK OFFICE
CERTIFICATE OF CORRECTION

PATENT NO. : 7,666,439 B2  Page 1 of 1
APPLICATION NO. : 11/507231
DATED : February 23, 2010
INVENTOR(S) : Hsien-Jue Chu et al.

It is certified that error appears in the above-identified patent and that said Letters Patent is hereby corrected as shown below:

Column 15, lines 21, 23 and 31, the bacterin "Mycoplasma pneumoniae" for each occurrence in Claim 1 should read --Mycoplasma hyopneumoniae--.

Signed and Sealed this

Eleventh Day of May, 2010

David J. Kappos
*Director of the United States Patent and Trademark Office*